United States Patent
Rao et al.

(10) Patent No.: US 8,159,286 B2
(45) Date of Patent: Apr. 17, 2012

(54) SYSTEM AND METHOD FOR TIME-TO-VOLTAGE CONVERSION WITH LOCK-OUT LOGIC

(75) Inventors: Naresh Kesavan Rao, Clifton Park, NY (US); Brian David Yanoff, Niskayuna, NY (US); Yanfeng Du, Rexford, NY (US); Jianjun Guo, Ballston Spa, NY (US)

(73) Assignee: General Electric Company, Niskayuna, NY (US)

( * ) Notice: Subject to any disclaimer, the term of this patent is extended or adjusted under 35 U.S.C. 154(b) by 757 days.

(21) Appl. No.: 12/199,020

(22) Filed: Aug. 27, 2008

(65) Prior Publication Data

US 2009/0128216 A1 May 21, 2009

Related U.S. Application Data

(60) Provisional application No. 60/978,283, filed on Oct. 8, 2007.

(51) Int. Cl.
*H03K 5/00* (2006.01)
(52) U.S. Cl. .................. 327/554; 327/558; 327/337
(58) Field of Classification Search .......... 327/336–337, 327/551–559
See application file for complete search history.

(56) References Cited

U.S. PATENT DOCUMENTS

| | | | |
|---|---|---|---|
| RE34,295 E * | 6/1993 | Shibuya et al. ............... | 341/133 |
| 5,621,406 A * | 4/1997 | Goetzinger et al. .......... | 341/120 |
| 5,696,458 A | 12/1997 | Tumer et al. | |
| 6,333,648 B1 | 12/2001 | Tumer | |
| 6,621,084 B1 | 9/2003 | Wainer et al. | |
| 6,683,462 B2 * | 1/2004 | Shimizu .................... | 324/658 |
| 6,909,672 B2 | 6/2005 | Rao | |
| 7,126,386 B2 | 10/2006 | Tumer et al. | |
| 7,297,955 B2 | 11/2007 | Amemiya et al. | |
| 2004/0056202 A1 | 3/2004 | Rao | |
| 2006/0071174 A1 | 4/2006 | Spartiotis et al. | |
| 2007/0057699 A1 | 3/2007 | Tumer et al. | |
| 2007/0235657 A1 | 10/2007 | He et al. | |
| 2008/0042070 A1 | 2/2008 | Levin | |

FOREIGN PATENT DOCUMENTS

| | | |
|---|---|---|
| DE | 102005020503 A1 | 11/2006 |
| WO | 2005065333 A2 | 7/2005 |
| WO | 2006039494 A2 | 4/2006 |

(Continued)

OTHER PUBLICATIONS

PCT International Search Report-5, dated Apr. 15, 2010.

(Continued)

*Primary Examiner* — Dinh T. Le
(74) *Attorney, Agent, or Firm* — Marie-Claire B. Maple

(57) ABSTRACT

An event time stamping system comprising a current source, an integrator comprising an input and an output, and configured to output a voltage proportional to the length of time the current source is coupled to the input, and one or more switches configured to couple the current source to the input of the integrator upon receipt of an event signal and configured to de-couple the current source from the input of the integrator upon receipt of a control trigger. The system further comprises a lock-out signal generator configured to generate a lock-out signal, and a controller coupled to the one or more switches, wherein the controller is configured to generate the control trigger based on the lock-out signal to ensure a minimum integration time.

17 Claims, 8 Drawing Sheets

FOREIGN PATENT DOCUMENTS

WO    2007111912 A2    10/2007

OTHER PUBLICATIONS

PCT International Search Report-6, dated Apr. 21, 2010.

Tümer et al., "Preliminary Results Obtained From a Novel CdZnTe Pad Detector and Readout ASIC Developed for an Automatic Baggage Inspection", Nuclear Science Symposium Conference Record, IEEE, vol. 1, Lyon, France, Oct. 15-20, 2000, pp. 4-36 to 9-36.

Matteson et al., CZT Detectors Read Out With the RENA-2 ASIC, Nuclear Science Symposium Conference Record, IEEE, vol. 1, Puerto Rico, Oct. 23, 2005, pp. 211-216.

De Geronimo et al., "Advanced Readout ASICs for Multielement CZT Detectors," International Society for Optical Engineering, 2002, ISSU 4784, pp. 105-118.

Schulman, "Si, CdTe and CdZnTe radiation detectors for imaging applications," 2006, Helsinki, Finland.

Moss et al., "Performance of multi-element CdZnTe detectors," Proc. SPIE, vol. 3768, 1999, pp. 320-329.

Shikhaliev, "Tilted angle CZT detector for photon counting/energy weighting x-ray and CT imaging," Institute of Physics Publishing, Phys. Med. Biol. vol. 51, 2006, pp. 4267-4287, IOP Publishing Ltd, United Kingdom.

Iwanczyk et al., "Photon Counting Energy Dispersive Detector Arrays for X-ray Imaging," 2007 IEEE Nuclear Science Symposium Conference Record, pp. 2741-2748.

Zocca et al., "A Mixed Continuous-Pulsed Reset Technique for Digitized Preamplifiers of Radiation Signals," 2005 IEEE Nuclear Science Symposium Conference Record, pp. 382-386.

PCT International Search Report dated Sep. 11, 2009.

\* cited by examiner

SYSTEM AND METHOD FOR TIME-TO-VOLTAGE CONVERSION WITH LOCK-OUT LOGIC

CROSS-REFERENCE TO RELATED APPLICATION

This application claims the benefit of prior U.S. Provisional Application Ser. No. 60/978,283 filed Oct. 8, 2007, and which is incorporated herein in its entirety by reference.

GOVERNMENT RIGHTS NOTICE

This invention was made with government support under grant number HSHQDC-06-C-00089 awarded by the US Dept of Homeland Security. The government has certain rights in the invention.

BACKGROUND OF THE INVENTION

Embodiments of the invention relate generally to radiation detectors and, more particularly, to an apparatus and method for acquiring and processing electronic data from a radiation detector.

In the fields of security screening and medical imaging, non-invasive imaging techniques employing radiation detectors have gained importance due to benefits that include unobtrusiveness, ease, and speed. A number of non-invasive imaging techniques exist today. Single-photon-emission computed tomography (SPECT) imaging and x-ray computed tomography (CT) imaging are two examples.

At least two factors explain the increased importance of radiation detectors in security screening: an increase in terrorist activity in recent years, and an increase in the number of travelers. The detection of contraband, such as explosives and radioactive materials, being transported in luggage, cargo containers, and small vehicles and taken onto various means of transportation has become increasingly important. To meet the increased need for such detection, advanced systems have been developed that can not only detect suspicious articles being carried in luggage and other containers but can also determine whether or not the articles contain explosives or radioactive materials.

There is also a need for high-resolution gamma radiation detectors which can detect radioactive materials from a variety of sources. To gain widespread use, these radiation detectors must be economical, easily portable, and have low-power consumption. Semiconductor materials, such as cadmium-telluride (CdTe) and cadmium-zinc-telluride (CZT) crystals have applicability for compact radiation detectors. CdTe and CZT detectors have been shown to exhibit good energy resolution, especially as compared to scintillator-based detectors. Since they are direct conversion devices (i.e., convert radioactive particles, such as photons, directly into electronic signals), CdTe and CZT detectors eliminate the need for bulky photomultiplier tubes. Furthermore, CdTe and CZT radiation detectors do not require cryogenic cooling, as do high-purity germanium radiation detectors.

SPECT and CT imaging systems can incorporate such semiconductor, or solid state, radiation detector technology. CT systems are capable of acquiring mass and density information (as well as materials-specific information, such as an effective atomic number) on items within a piece of luggage. Although object density is an important quantity, surrogates such as "CT number" or "CT value" which represent a linear transformation of the density data, may be used as the quantity indicative of a threat. Features such as mass, density, and effective atomic number embody derived quantities such as statistical moments, texture, etc. of such quantities.

In CT imaging systems, an x-ray source emits a fan-shaped beam towards a subject or an object, such as, for example, a patient or piece of luggage. Hereinafter, the terms "subject" and "object" shall include anything capable of being imaged. The beam, after being attenuated by the object, impinges upon an array of radiation detectors. The intensity of the attenuated beam radiation received at the detector array is typically dependent upon the attenuation of the x-ray beam by the object. Each detector element of the detector array produces a separate electrical signal indicative of the strength of the attenuated beam received by each detector element. The electrical signals are transmitted from the detector array to a data processing system for analysis which ultimately produces an image.

Typically, in SPECT imaging systems, a gamma camera or similar radiation detector locates radiation emitted from a subject such as a patient, or an object such as a piece of luggage containing a radioactive substance. As above, "subject" and "object" are used interchangeably. When imaging a patient, a gamma-ray-emitting tracer material is administered to the patient. Typically, the tracer material is absorbed by the organ of interest to a greater degree than by other organs. In these systems, each element of the detector array produces a signal in relation to the localized intensity of the radiation emitted from the object. As with conventional x-ray imaging, the strength of the emission signal is attenuated by the interlying object or body part. Each element of the detector array produces a separate electrical signal indicative of the photon impinging upon the detector element. The electrical signals are transmitted from the detector assembly to a data processing system for analysis, which ultimately produces an image.

In SPECT imaging, a plurality of images is acquired at various angles around the area of interest. To acquire the images, the gamma camera is rotated around the patient. Generally, in transaxial tomography, a series of 2-D images, or views, are taken at equal angular increments around the patient. Typically, projections are acquired every 3-6 degrees. In some cases, a full 360 degree rotation is used to obtain an optimal reconstruction. Multi-head gamma cameras can provide accelerated image acquisition. For example, a dual-head camera can be used with detectors spaced 180 degrees apart, allowing two projections to be acquired simultaneously, with each head requiring 180 degrees of rotation. Triple-head cameras with 120 degree spacing are also used.

The series of views around the patient are reconstructed to form transaxial slices, or slices across the axis of rotation. The reconstruction is performed by a computer, which applies a tomographic reconstruction algorithm to the multiple views, yielding a 3-D dataset. This dataset may then be manipulated to show thin slices along any chosen axis of the body, similar to those obtained from other tomographic techniques, such as CT and PET.

A gamma camera radiation detector assembly may employ a multi-channel collimator and gamma ray detector to convert energy from the gamma ray photon into an electrical signal, which can be interpreted to locate the position of the gamma ray interaction in a planar detector. Gamma cameras may also include a large scintillation crystal responsive to radiation stimuli, such as gamma rays, emitted by the patient, and an array of photomultiplier tubes optically coupled to the crystal. In operation, the gamma rays emitted by the patient in the direction of the detector are collimated onto the crystal. Each gamma ray photon cloud that interacts with the crystal produces multiple light events that are detected by the photomultipliers near the point of interaction. Each light event detected by the photomultipliers produces an electrical signal. The electrical signals from the photomultiplier array are combined to provide an estimate of the location of the gamma ray emission. Analog and digital processing of the signal results in the generation of an image from the acquired data.

However, gamma cameras may also employ semiconductor detector elements, such as cadmium-zinc-telluride (CZT) elements, to replace the scintillator/photomultiplier system. CZT detector elements convert the signal from gamma ray photons directly into an electronic signal. By eliminating the light conversion step needed in scintillator/photomultiplier cameras, a gamma camera using semiconductor radiation detectors may exhibit higher signal to noise ratio, and increased sensitivity which can result in greater energy level resolution and better imaging contrast resolution.

SPECT and CT imaging systems incorporating semiconductor detector array technology may be able to provide compositional analysis of tissue using spectroscopic x-ray imaging while improving overall image quality and reducing the x-ray dose to the patient. Recent advances in the development cadmium-zinc-telluride (CZT) detectors and other direct conversion (i.e. semiconductor) detectors have extended the application of such detectors to medical imaging (i.e., SPECT and CT systems), security screening, nuclear experimentation, as well as to oil exploration and mining. As these detectors find more uses, increasing demands are placed on the electronic components of the detectors. The front end readout electronics or data acquisition system for a CZT detector is generally expected to exhibit low-noise, high linearity, wide dynamic range, and good drive capability. In addition to these requirements, portable systems may also demand data acquisition systems that are low-power, low-cost, with a high channel count.

Primarily, front end readout electronics capture two pieces of information from the radiation detector: the energy level of the radiation and the timing of the detection. While the energy level indicates the energy spectrum of the radiation, timing information is used to determine the depth of interaction so as to provide the full 3D position sensitivity needed for image reconstruction. There have been several application-specific integrated circuits (ASICs) developed to function as the front end readout electronics for radiation detectors. Typically, these ASICs have high power consumption and only provide analog outputs, making it necessary to provide an external digitizer typically at increased cost and decreased reliability. Additionally, some of these recently developed readout ASICs may offer incomplete information as to the energy level or timing of the detection.

It would be desirable to have a data acquisition system for radiation detectors that can operate at low power, with little noise, offer complete energy level and time discrimination capabilities, and provide digital outputs.

BRIEF DESCRIPTION OF THE INVENTION

According to one aspect of the invention, an event time stamping system comprising a current source, an integrator comprising an input and an output, and configured to output a voltage proportional to the length of time the current source is coupled to the input, and one or more switches configured to couple the current source to the input of the integrator upon receipt of an event signal and configured to de-couple the current source from the input of the integrator upon receipt of a control trigger. The system further comprises a lock-out signal generator configured to generate a lock-out signal, and a controller coupled to the one or more switches, wherein the controller is configured to generate the control trigger based on the lock-out signal to ensure a minimum integration time.

In accordance with another aspect of the invention, a method of manufacturing that includes providing a current source, providing an operational transconductance amplifier having an input and an output, coupling an integrating capacitor between the input and the output of the amplifier, and coupling one or more switches between the current source and the integrating capacitor. The method further includes coupling a controller to the one or more switches, and configuring the controller to control the one or more switches to de-couple the current source from the integrating capacitor after at least a minimum integration time.

According to yet another aspect of the invention, a time-to-voltage converter comprising a current source, a feedback capacitor, an operational transconductance amplifier having an output coupled to the feedback capacitor, and one or more switches configured to couple the current source to the feedback capacitor upon receipt of an event trigger, and configured to de-couple the current source from the feedback capacitor after a minimum determined time period.

These and other advantages and features will be more readily understood from the following detailed description of preferred embodiments of the invention that is provided in connection with the accompanying drawings.

DETAILED DESCRIPTION OF EXEMPLARY EMBODIMENTS

The operating environment of the invention is described with respect to both computed tomography (CT), and single photon emission computed tomography (SPECT) imaging systems. However, it will be appreciated by those skilled in the art that the invention is equally applicable for use with other systems, such as portable radiation detectors. Moreover, the invention will be described with respect to the detection and conversion of gamma ray radiation. However, one skilled in the art will further appreciate that aspects of the invention may be equally applicable to the detection and conversion of other high frequency electromagnetic energy.

Figure 1:
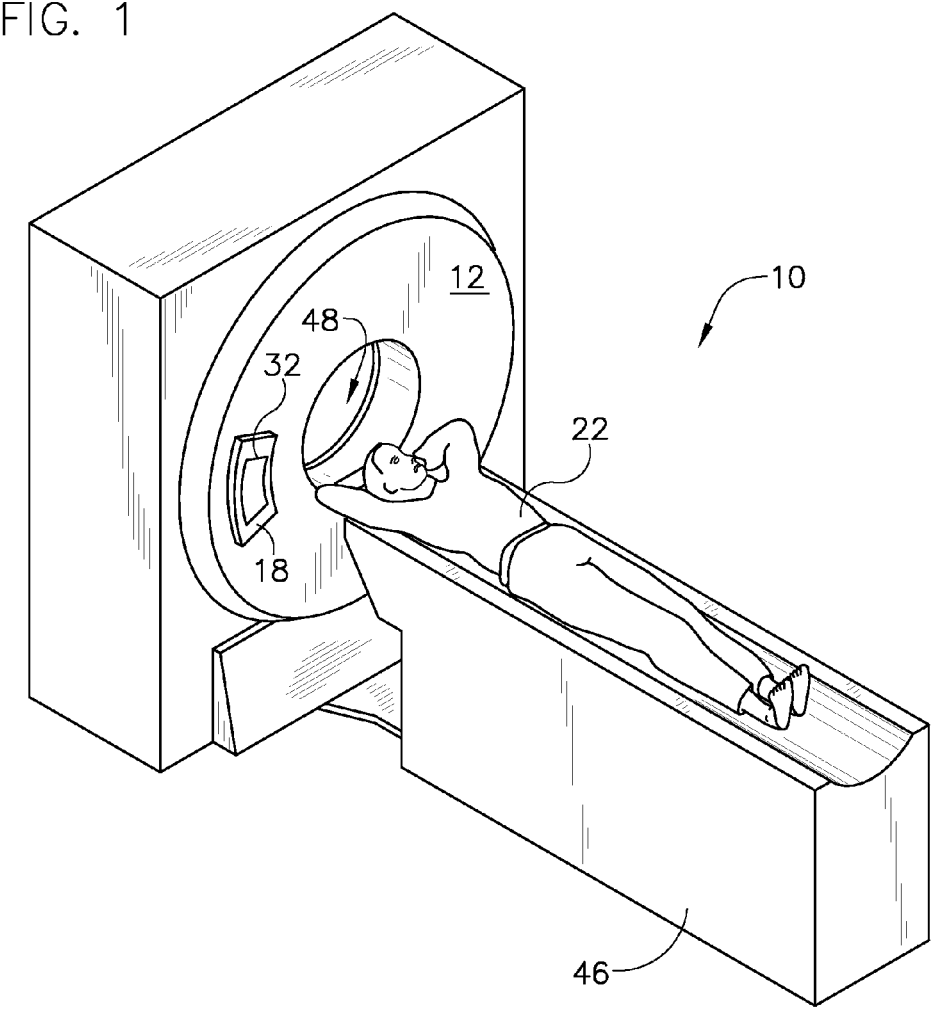
FIG. 1 is a pictorial view of a SPECT imaging system according to an embodiment of the invention.
Figure 2:
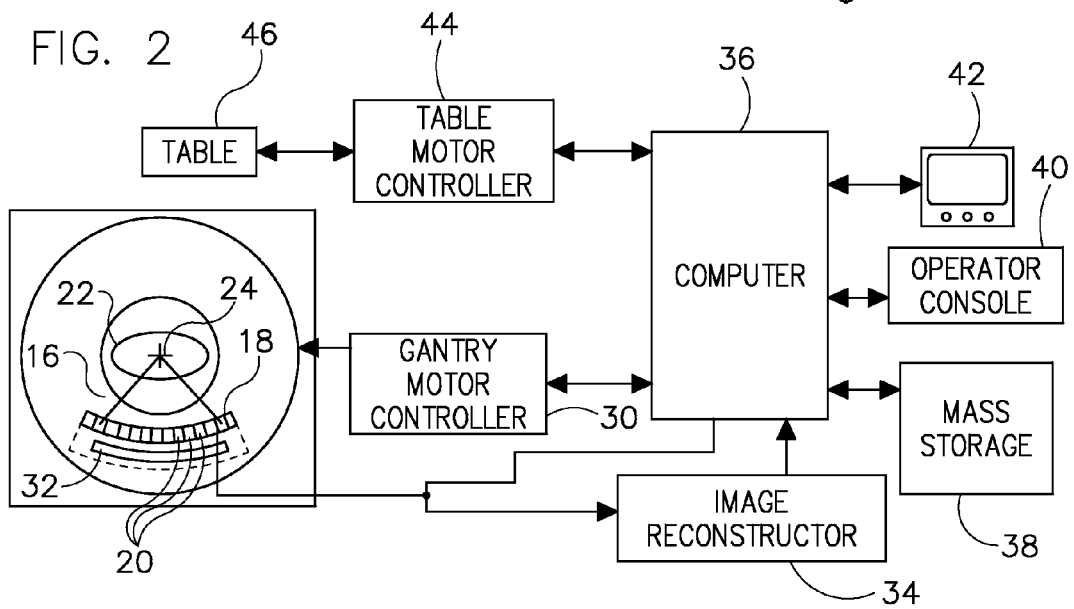
FIG. 2 is a block diagram of the system illustrated in FIG. 1.

Referring to FIG. 1, a single photon emission computed tomography (SPECT) imaging system 10 incorporating an embodiment of the invention is shown as including a gantry 12. Gantry 12 has a gamma ray detector 18 that detects photons from gamma rays emitted from the subject 22. Although the subject 22 is shown as a person, it is to be appreciated that the SPECT imaging system 10 may be configured for industrial applications such as inspection imaging, or to image items of interest from a security perspective, such as, for example, luggage or packages. Referring now to FIG. 2, detector assembly 18 is formed by a plurality of radiation detectors 20 and data acquisition systems (DAS) 32. The plurality of radiation detectors 20 sense the gamma-rays 16 that pass through a subject 22, and DAS 32 converts the data to digital signals for subsequent processing. Each detector 20 produces an analog electrical signal that represents the intensity of an impinging gamma ray photon cloud and hence the attenuated photon cloud as it passes through the subject 22.

During a scan, gantry 12 and the components mounted thereon rotate about a center of rotation 24. Rotation of gantry 12 is governed by a gantry motor controller 30 of SPECT system 10. Gantry motor controller 30 controls the rotational speed and position of gantry 12. An image reconstructor 34 receives sampled and digitized data from DAS 32 and performs high speed reconstruction. The reconstructed image is applied as an input to a computer 36, which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, and gantry motor controller 30. In addition, computer 36 operates a table motor controller 44 which controls a motorized table 46 to position subject 22 and gantry 12. Particularly, table 46 moves subjects 22 through a gantry opening 48 of FIG. 1 in whole or in part.

Figure 3:
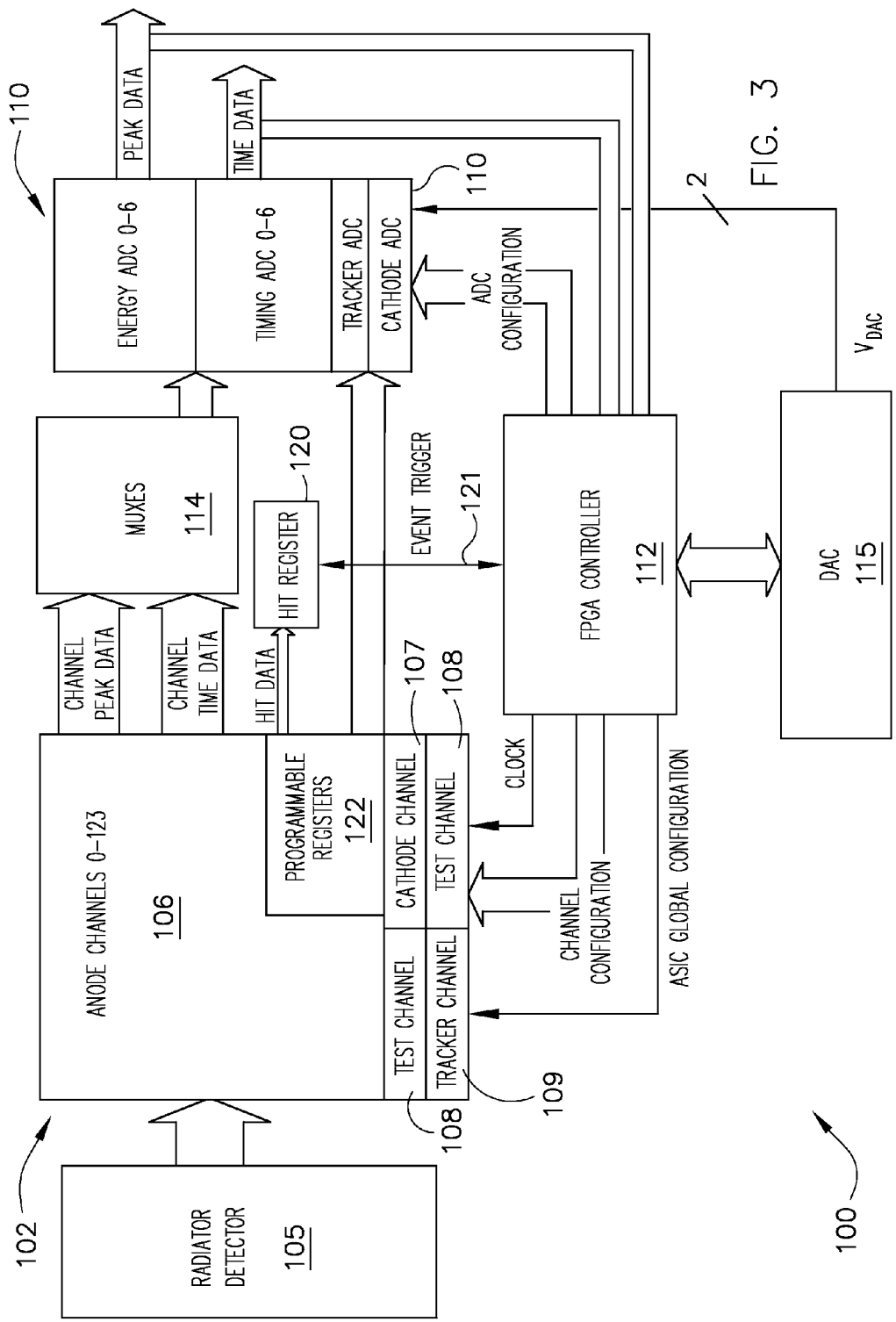
FIG. 3 is a block diagram of one embodiment of a data acquisition system for a semiconductor radiation detector useable in the system illustrated in FIG. 1.

FIG. 3 shows a schematic block diagram of an electronic system 100 for the acquisition of data from a semiconductor, or solid state, radiation detector according to an embodiment of the invention. Electronic system 100 includes a low-noise, low-power, multi-channel readout ASIC 102 having one hundred and twenty-six anode channels 106, 108 and two cathode channels 107, 108. Each channel 106-109 has an energy discriminating circuit (discussed below with respect to FIG. 6) and a time discriminating circuit (discussed below with respect to FIG. 8). The ASIC 102 also has built-in analog to digital converters (ADCs) 110, or digitizers, to digitize the signal from energy sub-channels 200 in FIG. 6 and timing sub-channels 250 in FIG. 8. In one embodiment, ASIC 102 is fabricated using a CMOS process, achieving 20 nanosecond timing resolution while consuming less than 1 mW per channel and adding less than 4.5 keV (FWHM) equivalent noise at two picofarads parasitic capacitance to the anode energy reading. Electronic noise for cathode readings generally adds less than seven keV at ten picofarads parasitic capacitance.

The block diagram of FIG. 3 shows an embodiment of the front end readout electronics for a data acquisition system 100 that could be used in conjunction with a semiconductor, radiation detector 105, such as a CZT detector. One hundred twenty-four channels of the anode channels 106 are configured to interface with anodes (not shown) of detector 105, and cathode channel 107 is configured to interface with a cathode (not shown) of detector 105. There are two test channels 108 (one anode and one cathode) to facilitate stand-alone testing of ASIC 102. Tracker channel 109 is configured to monitor the variation of ASIC 102 parameters with environmental conditions and to provide calibration data for a digital controller 112.

Tracker channel 109 allows the DAS to compensate for the effects of temperature changes on ASIC 102 circuitry. Controller 112, which includes temperature tracking circuitry, sends a temperature-insensitive reference signal (e.g., a bandgap signal) to the input of all input channels 106-109. The energy and timing information associated with the reference signal is processed and digitized by the plurality of ADCs 110. Controller 112 tracks the variation in the digital output of the ASIC 102 from a reference signal output from channels 106-109 and generates correction coefficients. The correction coefficients may be then applied to subsequent digital outputs from channels 106-109 to eliminate or reduce temperature-induced error.

In the embodiment of FIG. 3, a field programmable gate array (FPGA) acts as digital controller 112. Controller 112 may be configured to minimize energy usage of the ASIC 102 by operating the ASIC 102 at a nominal frequency, for example, from one to two megahertz, before a signal is received from the radiation detector 105. While ASIC 102 is waiting for a signal from the radiation detector 105, controller 112 operates in a quiet mode during which it has little or no communication with ASIC 102. Quiet mode operation is employed to minimize any signal noise that might introduce error into the energy and timing measurements performed by ASIC 102. After a signal, such as a HIT signal, is indicating detected radiation is received by ASIC 102 from the detector, controller 112 goes into an active mode in which the ASIC clock frequency may increase from the nominal frequency to about twenty megahertz to minimize the time needed to generate a digital output. The period during which ASIC 102 generates a digital output is called "dead time" because the ASIC cannot process subsequent detector signals during this time. Speeding up the ASIC clock after a HIT signal reduces dead time. In active mode, processing circuits (not shown) within controller 112 are enabled, and multiplexers 114 in ASIC 102 are directed to assign energy and timing signals from the anode channels 106 and cathode channel 107 to specific ADCs 110. Controller 112 then causes a digital-to-analog converter (DAC) 115 to generate an analog signal ramp, or reference signal, used to digitize the energy and timing signals. Following digitization, controller 112 initiates the generation of waveforms used to reset ASIC 102 to quiet mode in which ASIC 102 is ready to receive and process new signals from radiation detector 105 and in which the ASIC 102 clock frequency is once again set to the nominal frequency.

A single gamma ray may deposit energy into multiple detector channels. Radiation detected by the detector is commonly referred to as an "event." Typically, for any radiation event, each anode channel 106 that registers a signal raises a digital HIT flag, which is stored in a HIT register 120. The digital HIT flag triggers the time stamping circuitry to sample the event time, while the energy channel measures the level of the charge deposit. The hits recorded in the HIT register 120 are combined to output a control trigger, or event trigger 121, to controller 112. In an embodiment of the invention, HIT register 120 contains one-hundred twenty-eight bits, one bit for each ASIC 102 channel. Initially, the bits would be set to a state indicating no hits detected. Once radiation is detected on a particular channel, the corresponding bit in HIT register 120 would transition low to high, or high to low. By querying HIT register 120 and reading all one-hundred twenty-eight bits, controller 112 determines the number of hits detected and on which channel the hit occurred.

In operation, upon receipt of event trigger 121 from ASIC 102, controller 112 causes DAC 115 to generate a reference signal in the form of a signal ramp to begin data conversion, in which the analog energy level and timing information are digitized or converted to digital form. Event trigger 121 is de-asserted during digitization, then re-asserted when digitization is complete. Re-assertion of event trigger 121 discontinues the ramp signal from DAC 115. Upon completion of digitization, controller 112 resets ASIC and de-asserts event trigger 121, readying ASIC 102 for the next event. The energy level information is preferably digitized with 12-bit resolution, which corresponds to a 4.5 keV energy resolution, and the timing information is preferably digitized to 10-bit resolution, which corresponds to a five nanosecond timing resolution. Multiple ASICs 102 may be tied to a single controller 112 and DAC 115 to achieve higher channel counts. For example, controller 112 can also synchronize the HIT data from multiple ASICs 102 to determine the energy level and timing of coincident radiation events that are simultaneously detected on different ASICs 102.

Figure 4:
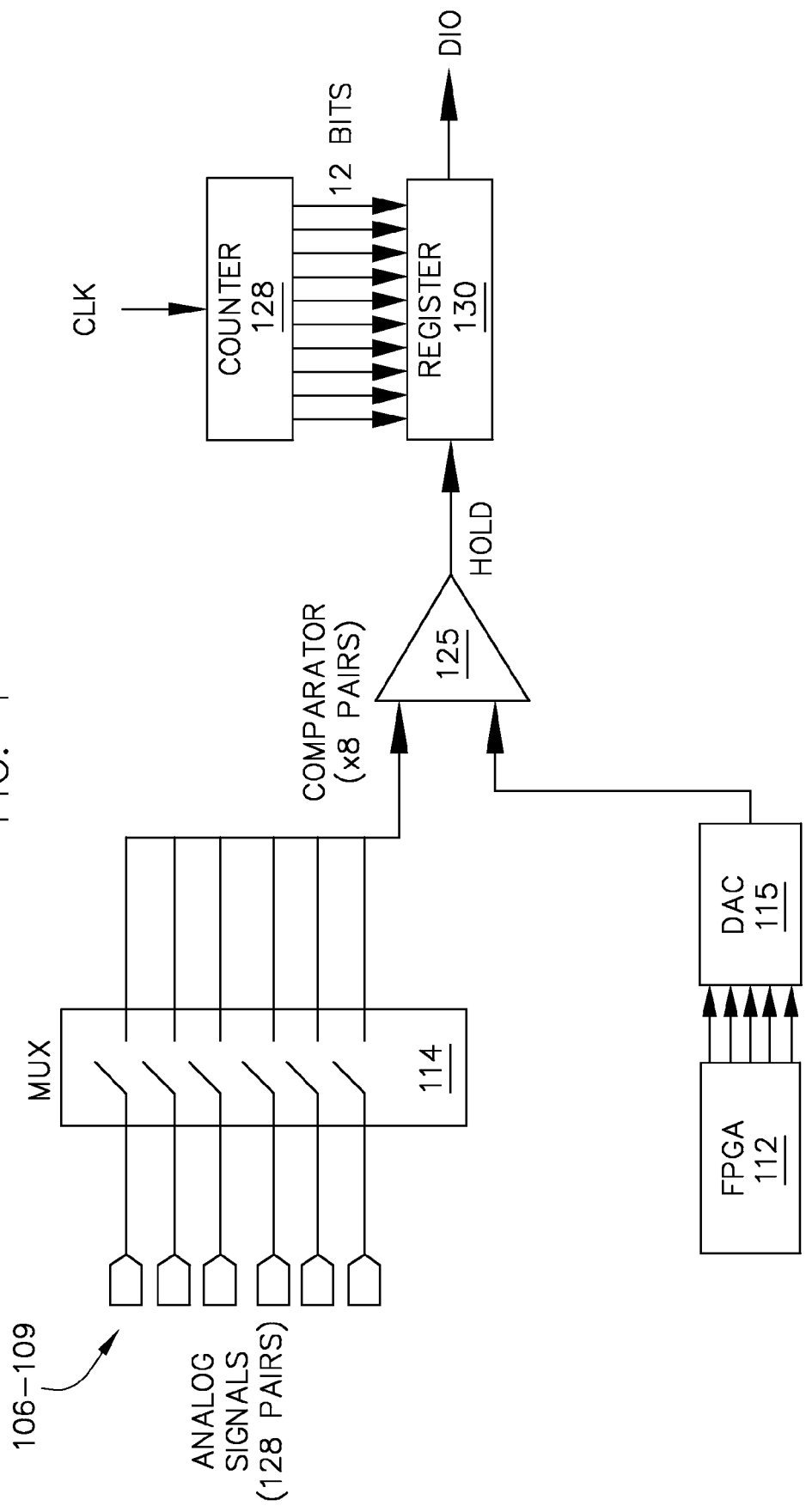
FIG. 4 is a block diagram of an analog-to-digital converter circuit useable in the system illustrated in FIG. 3.

Referring to FIG. 4, a schematic block diagram of an analog-to-digital converter is shown. The analog signal from a separate digital-to-analog conversion (DAC) 115 chip, controlled by digital controller 112, is used by an analog-to-digital converter (ADC) 110 in FIG. 3 circuit in ASIC 102 to generate the ASIC's digital output. The analog energy and timing signals from anode channels 106 and cathode channel 107 are routed to a pair of comparators 125 having two inputs. The inputs to one comparator include the output of the energy discriminating circuit and an output of DAC 115. The other comparator receives the output of the time discriminating circuit and an output of DAC 115. Controller 112 simultaneously starts a counter 128 and instructs DAC 115 to supply a signal ramp, or reference signal, to the pair of comparators 125. When the voltage from DAC 115 reference signal increases beyond the voltage of the energy signal on the comparator 125, it causes the comparator 125 output to trip, latching the counter 128 value at the time comparator 125 tripped into register 130. The value on counter 128 that is latched into register 130 upon comparator 125 tripping represents the digital value, or time stamp, of the analog energy signal. This process is repeated to obtain a digital value for the timing signal on the remaining comparator 125. The same reference signal may be used for the digitization of both energy and timing signals. Furthermore, if the system contains multiple ASICs 102 tied to the digital controller 112, a common reference signal may be used to generate the digital outputs for all of the ASICs 102 tied to that controller 112.

The ASIC's built-in ADC 110 circuitry includes eight pairs of ramp-based comparators 125 as shown in FIG. 4. Each pair of comparators 125 process energy and time information from one channel. It is contemplated that one pair of comparators 125 may be dedicated to cathode channels 107, 108 and another pair of comparators 125 may be dedicated to tracker channel 109. When an anode channel 106 registers a hit, controller 112 reads the HIT register 120, assigns each hit channel to a comparator 125 pair, and controls digitization by initiating an analog ramp from DAC 115.

Referring to FIGS. 3 and 4, ASIC 102 includes a plurality of programmable registers 122. In one embodiment, there are two hundred and fifty-six programmable registers 122 on ASIC 102, sixty-eight of which are reserved for channel specific actions such as bus connect, channel enable/disable, and digital test bits. The remaining one hundred and eighty-eight programmable registers 122 are used for waveform generation, testing, and channel configuration.

Channel configuration involves setting of certain parameters for the energy and time discrimination circuits. Those parameters include the setting of low-trim threshold, power supply level, shaping time constant, and channel connection to the multiplexer 114. Configuring each anode channel 106 separately increases the effectiveness of ASIC 102 by accounting for variation in electronic device properties across different channels. The low-trim threshold refers to the anode channel signal threshold voltage above which the signal is considered a valid hit. Anode signals below the low-trim threshold are considered to be noise or digital crosstalk. Because the radiation detector 105 elements connected to anode channels 106 exhibit variable leakage currents, it is more effective to be able to set the low-trim threshold separately for each anode channel 106.

Figure 5:
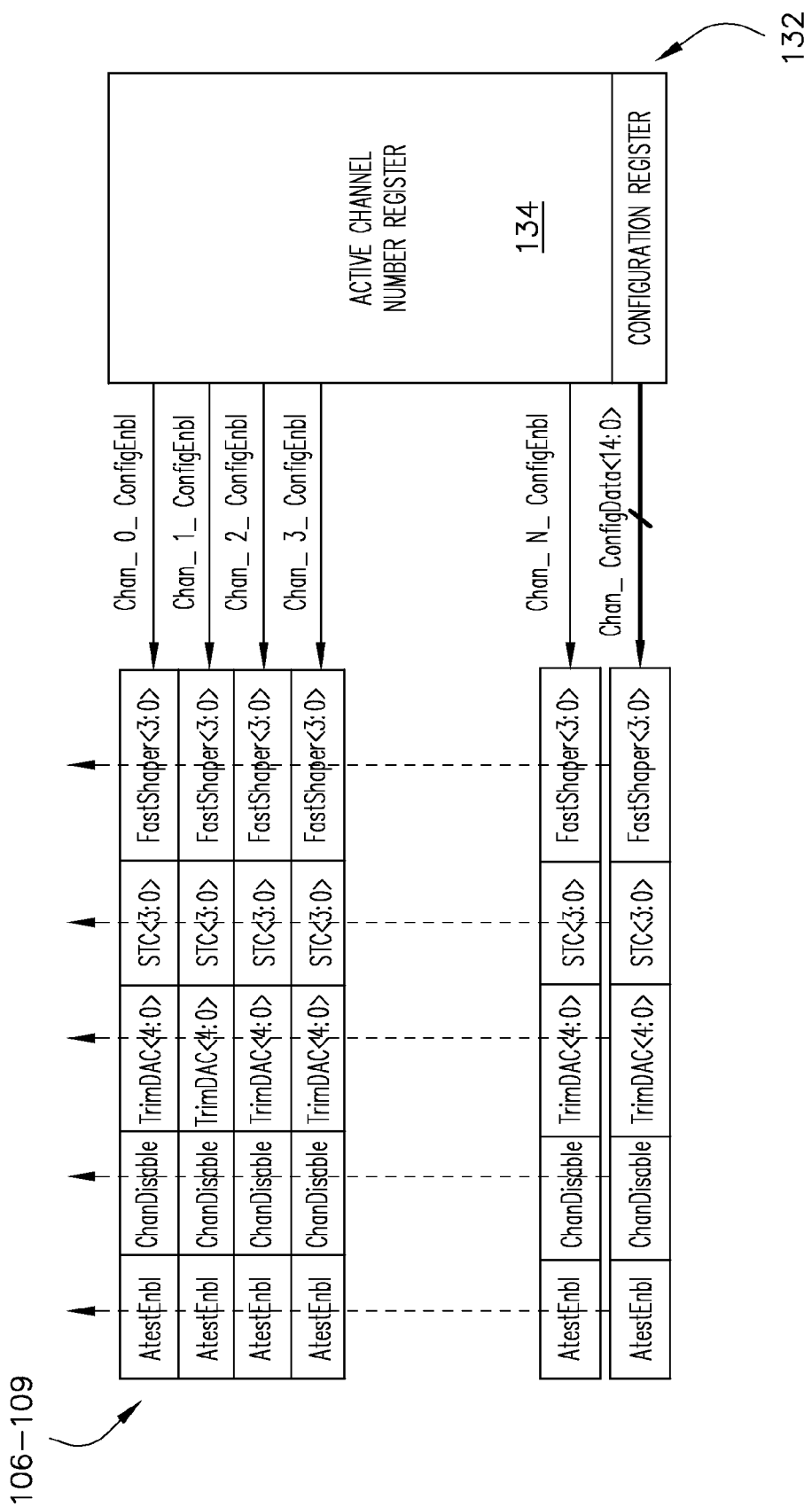
FIG. 5 is a block diagram of channel configuration registers useable in the system illustrated in FIG. 3.

FIG. 5 is a block diagram of channel configuration registers of ASIC 102 (shown in FIG. 3). All one hundred and twenty-eight anode and cathode channels 106-109 can be configured with just three dedicated registers 132, 134. ASIC 102 includes two configuration registers 132 containing the desired configuration parameters for the specific channel to be configured. Activate channel number register 134 contains the number of the channel to be configured. Using just three registers 132, 134 to configure all one hundred and twenty-eight anode and cathode channels simplifies the layout of ASIC 102 (in FIG. 3), especially when compared to readout devices that use a separate configuration register for each anode and cathode channel. Also, having just three registers dedicated to channel-specific configuration and just eight ADCs (110 in FIG. 3) results in fewer digital signals to analog sections of ASIC 102 when compared to readout devices with one ADC for each channel and with more configuration registers. Fewer signals between digital and analog sections of the chip decreases the amount of analog-to-digital crosstalk and the resulting noise. The simplified layout of the registers on ASIC 102 permits registers 132, 134 that are used for channel configuration to be aligned with registers dedicated to each ASIC channel 106-109. As a result, digital signals to and from the ASIC's channel registers run substantially perpendicular to the ASIC's analog signals, further minimizing analog-to-digital crosstalk.

Figure 6:
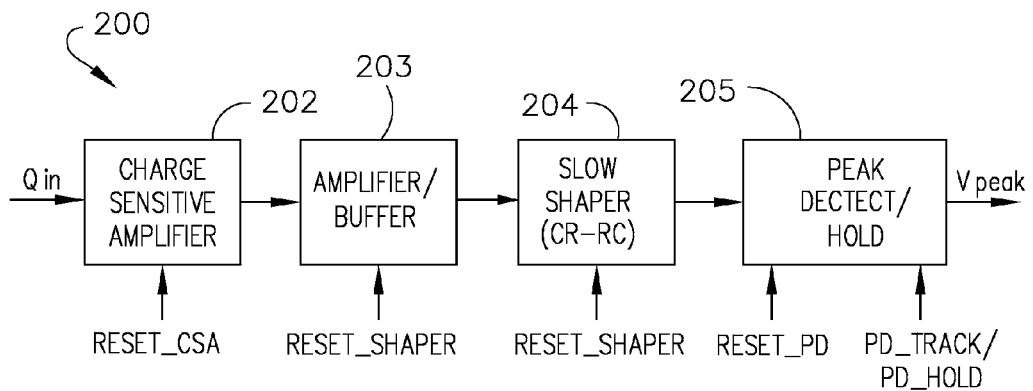
FIG. 6 is a block diagram of an energy discriminating circuit useable in the system illustrated in FIG. 3.

FIG. 6 is a block diagram illustrating an embodiment of an energy discriminating circuit 200 for ASIC 102. The energy discriminating circuit 200 is designed to measure a charge created in detector 105 (shown in FIG. 3) by absorption of a gamma ray. Energy discriminating circuit 200 collects a charge, $Q_{in}$, from the detector 105 that is amplified by a charge sensitive amplifier 202. The signal from charge sensitive amplifier 202 is amplified again in an amplifier/buffer 203, which provides isolation and gain to the signal to facilitate further processing. The shape of the charge pulse from amplifier/buffer 203 is modified by a slow shaper 204 to improve the signal-to-noise ratio by limiting the bandwidth and increasing the duration of the pulse for the subsequent pulse peak detection. One embodiment of the invention uses a first order CR-RC pulse shaper 204 with a programmable shaping time from 500 nanoseconds to four microseconds. The gain of shaper 204 can also be programmed to one of four possible values.

The peak detect/hold (PDH) circuit 205 then detects and holds the peak of the pulse output from slow shaper 204 for digitization. PDH circuit 205 extracts the peak value of the pulse and holds that peak value allowing for conversion of the analog signal to digital form. The peak detect signal is gated with a valid HIT signal. Without a valid HIT signal from the anode time discrimination circuitry, any peak detect signal would be ignored. The PDH circuit 205 also generates a digital peak-found signal when peak detect is complete to trigger an automatic transition from peak detect to peak hold mode.

Figure 7:
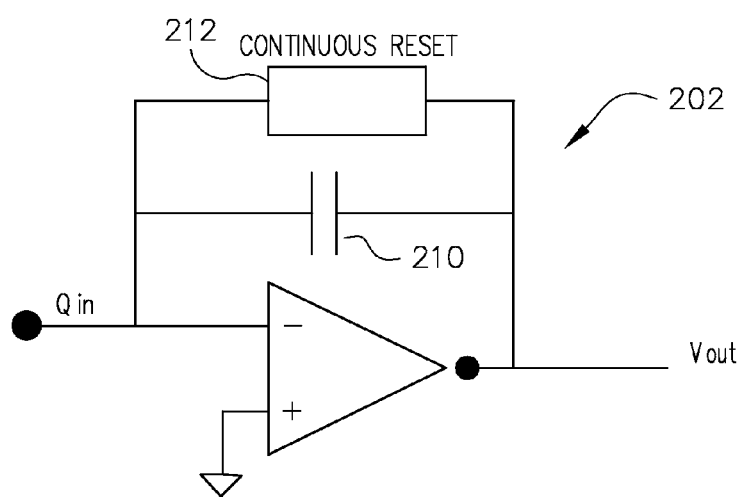
FIG. 7 is a schematic diagram of a charge-sensitive amplifier circuit for use in the energy discriminating circuit illustrated in FIG. 6.

In the embodiment of FIG. 7, a schematic diagram of charge sensitive amplifier (CSA) 202 of FIG. 6 is shown. CSA 202 integrates the charge $Q_{in}$ collected by the detector 105 (shown in FIG. 3) and converts it to a voltage. Typically the signal $Q_{in}$ from a semiconductor radiation detector 105, such as a CZT detector, is a quantity of charge delivered as a current pulse lasting from one nanosecond to ten microseconds, depending on the size and bias voltage of the detector. FIG. 7 illustrates one embodiment of CSA 202 that integrates charge on a feedback capacitor 210.

Another function of the CSA 202 is to minimize the amount of noise added to the signal. Typically, front end readout electronics for radiation detectors are generally expected to add no more than a few hundred electrons to the acquired signal. A continuous reset element 212, which is usually a resistive element, compensates for leakage current in DC-coupled detectors and prevents the CSA 202 from saturating. In an embodiment of the invention, anode leakage currents are typically about four-hundred fifty picoamps. For cathode channels, such as cathode channel 107 of FIG. 3, continuous reset element 212 may be eliminated since the signal $Q_{in}$ from the cathode channel is preferably AC-coupled to ASIC 102 (shown in FIG. 3) through a capacitor (not shown). Cathode leakage currents may be, for example, on the order of forty-five nanoamps.

Figure 8:
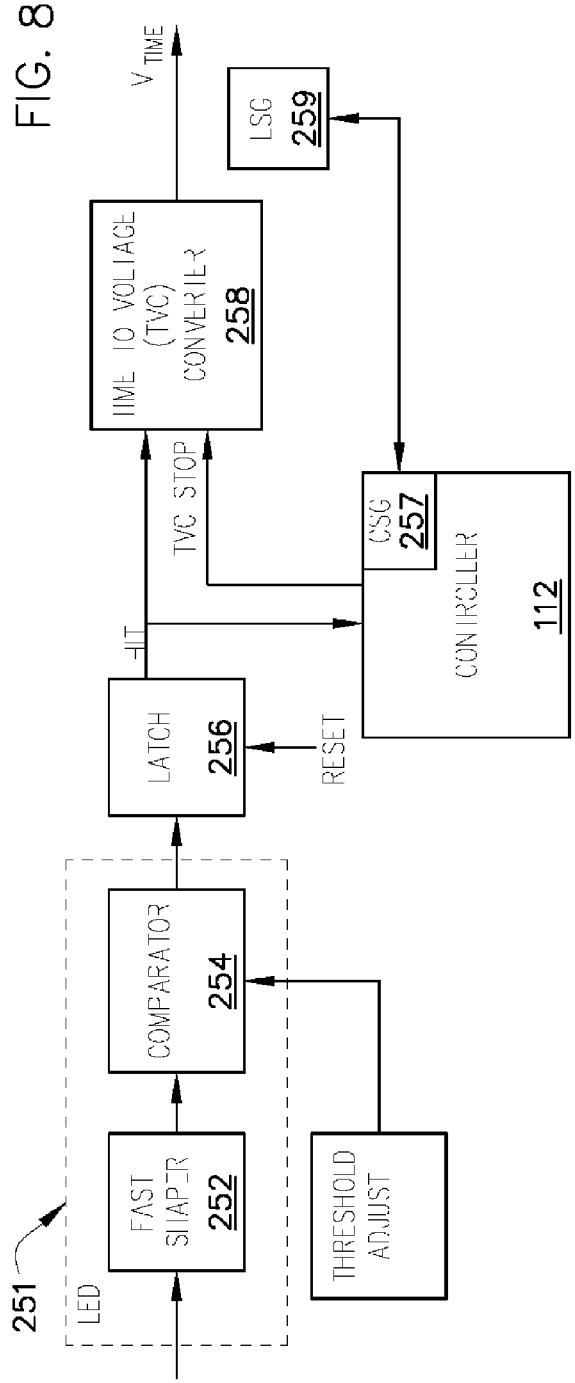
FIG. 8 is a block diagram of time discriminating circuit useable in the system illustrated in FIG. 3.

Referring to FIG. 8, a block diagram illustrating a time discriminating circuit 250 of ASIC 102 according to an embodiment of the invention is shown. Time discriminating circuit 250 serves two functions: to identify an event and raise a HIT flag, and to time stamp the event to within 20 nanoseconds FWHM (full width at half maximum). Thus, a single channel has two outputs: a digital HIT flag, and an analog time stamp signal. Time discriminating circuit 250 includes a leading edge discriminator (LED) 251 that raises a HIT flag when a gamma ray is detected. LED 251 includes a fast CR shaper 252 and an LED comparator 254. One embodiment of the CR shaper 252 includes a programmable resistor array to optimize jitter, and four-bit programmable shaping times from twenty-five nanoseconds to four-hundred nanoseconds.

Referring again to FIG. 8, the leading edge discriminator 251 and latch 256 are followed by a time-to-voltage converter (TVC) 258 that provides a voltage proportional to the event time. TVC 258 has two inputs: the HIT signal from latch 256, and the TVCStop signal from controller 112. As will be explained more fully below, the TVCStop signal is generated based on the state of a clock signal from a clock signal generator (CSG) 257 in controller 112 and on the state of a lock-out signal from a lock-out signal generator 259 (LSG) in ASIC 102 (in FIG. 3) at the time the HIT signal occurred. TVC 258 produces an analog output voltage that is a linear function of the time at which the HIT signal occurred.

Figure 9:
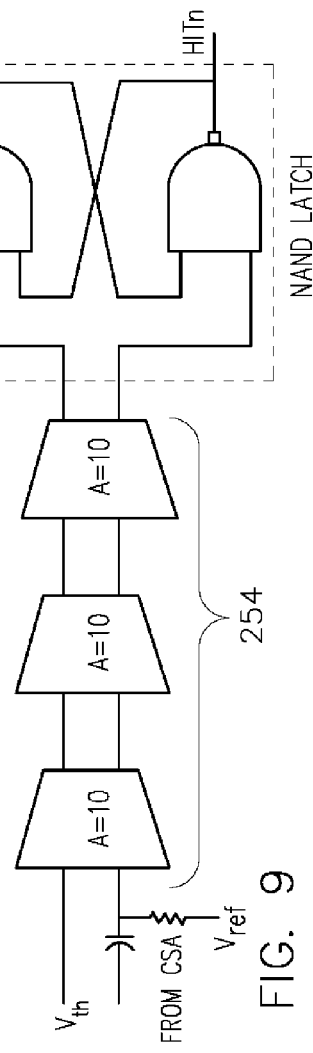
FIG. 9 is a block schematic diagram of a leading edge discriminator circuit for use in the time discriminating circuit illustrated in FIG. 8.

Referring to FIG. 9, a schematic diagram of the leading edge discriminator comparator 254 and latch 256, which raises the HIT flag described above. Other embodiments of the invention may use a constant fraction discriminator or a CR zero crossing discriminator. The three-stage comparator 254 of FIG. 9 provides an overall gain of about one thousand. Using three low-gain stages helps ensure linearity throughout the chain of amplifiers. NAND latch 256 provides a digital-compatible signal output. Typically, the baseline voltage is set close to mid-rail, and the threshold voltage is varied from 12 to 75 keV above the baseline voltage. In an embodiment of the invention, five bits are available to configure the threshold voltage. This configuration can be unique to a particular channel. The baseline and threshold voltages are reversed for the cathode channel 107 in FIG. 3.

Figure 10:
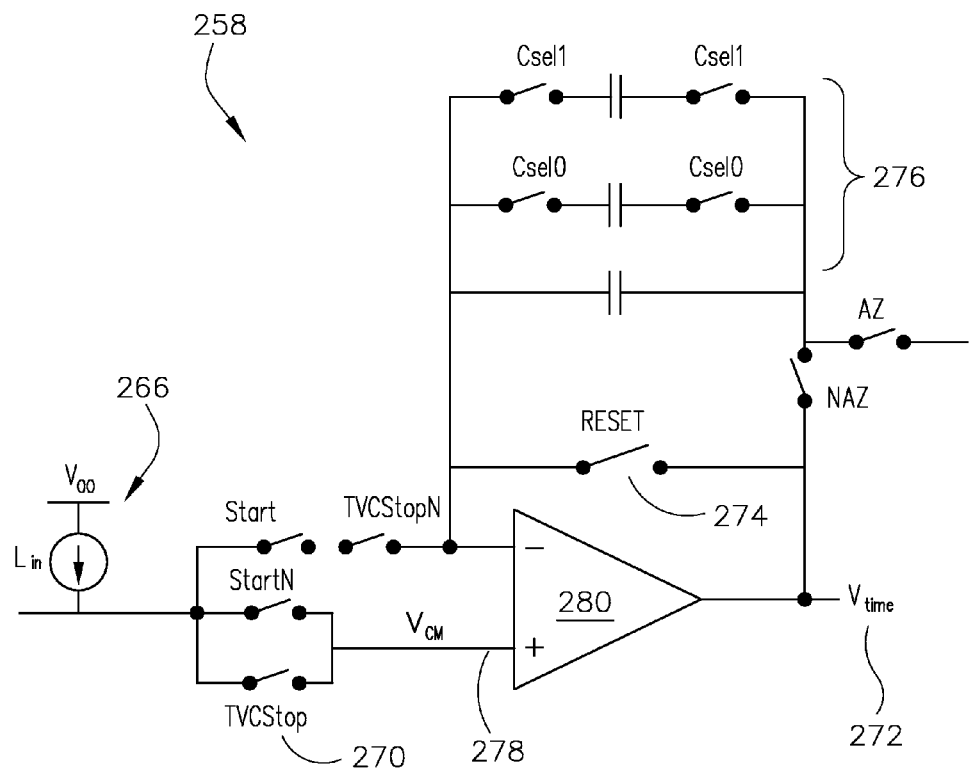
FIG. 10 is a block schematic diagram of a time-to-voltage converter circuit for use in the time discriminating circuit illustrated in FIG. 8.

FIG. 10 illustrates a schematic diagram of TVC 258 circuit realized as an integrator with a current source 266 that is turned on by the HIT signal from the timing circuit comparator 125 (shown in FIG. 4) and turned off by the closing of a TVCStop switch 270. The signal to close TVCStop switch 270 is normally generated by controller 112 on the next rising edge of the ASIC clock, according to an embodiment of the invention. The integrator includes an operational transconductance amplifier (OTA) 280, a bank of feedback capacitors 276 and a series of switches. The voltage at a TVC output 272 is proportional to the time of integration, the constant of proportionality being the ratio of the integration current and the capacitance.

A reset switch 274 is used to initialize a TVC 258. Current source 266 is connected to capacitor bank 276 during the period of integration. At other times, current source 266 is sunk to a common-mode node 278 of operational transconductance amplifier (OTA) 280. As mentioned above, integration commences with the receipt of a control trigger signal 121 indicating a radiation event (shown in FIG. 3). Current source 266 is connected to the integrator thereby charging one or more capacitors in capacitor bank 276. The voltage on capacitor bank 276 continues to rise during integration. Controller 112 includes a clock generator which produces a system clock signal for all ASICs 102 coupled to controller 112. At the next rising edge of the ASIC system clock, current source 266 is switched from the integrator to common-node 278. The system maintains the voltage level on capacitor bank 276 at the value when current source 266 was disconnected. With reference to FIGS. 4 and 10, the capacitor bank 276 voltage is routed by multiplexer 114 routes to an input of one of the ASIC comparators 125. DAC 115 provides the second input to comparator 125. As explained above, when the reference signal from DAC 115 ramps up, controller 112 starts a counter 128. When the reference signal voltage reaches the capacitor bank 276 voltage, the comparator 125 output trips latching the counter 128 value into a register 130. The register 130 value is the time stamp for the detected radiation.

In an embodiment of the invention shown in FIG. 10, capacitance values for capacitor bank 276 typically range from 250 femtofarads to one picofarad. Switches Csel0, Csel1 on either side of capacitors C0, C1 allow capacitors C0, C1 to be connected or disconnected from the circuit as necessary. Programming of two bits controlling capacitor switches Csel0, Csel1 enables selection of four capacitor values. As integration current is proportional to capacitance, the current has four possible values, typically ranging from 500 nanoamps to two microamps.

To prevent incomplete integration and reduce integral non-linearity (INL) errors, there is a minimum integration time. As will be explained below, a lock-out signal generator 259 (in FIG. 8) in ASIC 102 (in FIG. 2) generates a lock-out signal, which is a phase-shifted version of the clock signal provided by controller 112, to ensure that the minimum integration time requirement is met. The integration is started asynchronously by the control trigger signal indicating a radiation event and is terminated by the TVCStop command, which is generated by controller 112 and can be initiated by the positive-going edge of an ASIC integration clock signal. In the absence of a lock-out signal, this maintains a maximum integration period of one microsecond (i.e., the period of one clock cycle), but can lead to arbitrarily short integration periods if the HIT signal occurs too close to the rising edge of the clock. In one embodiment of the ASIC 102 (shown in FIG. 3), in which the clock signal frequency is one megahertz, a TVC lock-out signal is used to keep integration times between 250 nanoseconds and 1.25 microseconds.

Figure 11:
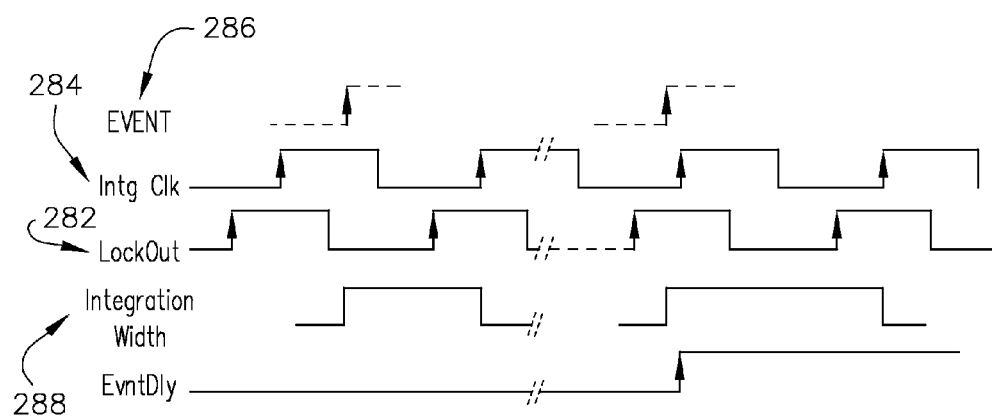
FIG. 11 is an illustration of a timing diagram for lock-out logic useable in the system illustrated in FIG. 3.

Referring to FIG. 11, a lock-out clock signal 282 is shown in quadrature with and leading an ASIC system clock signal, or integration clock signal 284. The phase shift between the integration clock signal 284 and the lock-out clock signal 282 represents the minimum integration time. For example, if the integration clock signal 284 and lock-out clock signal 282 have a one microsecond cycle time, the 90-degree phase shift illustrated in FIG. 11 translates into a 250 nanosecond minimum integration time. If an event 286 occurs before the rising edge of the lock-out clock signal 282, the integration continues until the next rising edge of the integration clock signal 284. This occurs irrespective of whether the event 286 occurs before or after the rising edge of the integration clock signal 284 and guarantees integration times between 250 nanoseconds and 750 nanoseconds, according to an embodiment of the invention. If the event 286 occurs after the rising edge of the lock-out clock signal 282, integration continues for an additional clock period ensuring a maximum integration time of 1.25 microseconds, while avoiding integration periods of less than 250 nanoseconds, while and the associated integral nonlinearity (INL) errors.

An N-bit counter (not shown) is used to track the location of the event 286 edge with respect to the integration clock signal 284 and the lock-out clock signal 282. Events 286 get one of four clock stamps generated by the N-bit counter. The clock stamps are stored in a circular buffer. The relative position of all hits is determined by the digitized integration width, or time stamp value, and the clock stamp. The N-bit counter is synchronized across all ASICs in the system and with controller 112 (in FIG. 3), and can confirm the validity of the time stamp and provide controller 112 (in FIG. 3) with information on an integration width 288 so that, when needed, the additional clock period of integration may be subtracted from the event 286 time stamp. Controller 112 (shown in FIG. 3) coordinates the lock-out state across multiple ASICs 102 (shown in FIG. 3) to determine the coincidence of each event 286 registered.

Figure 12:
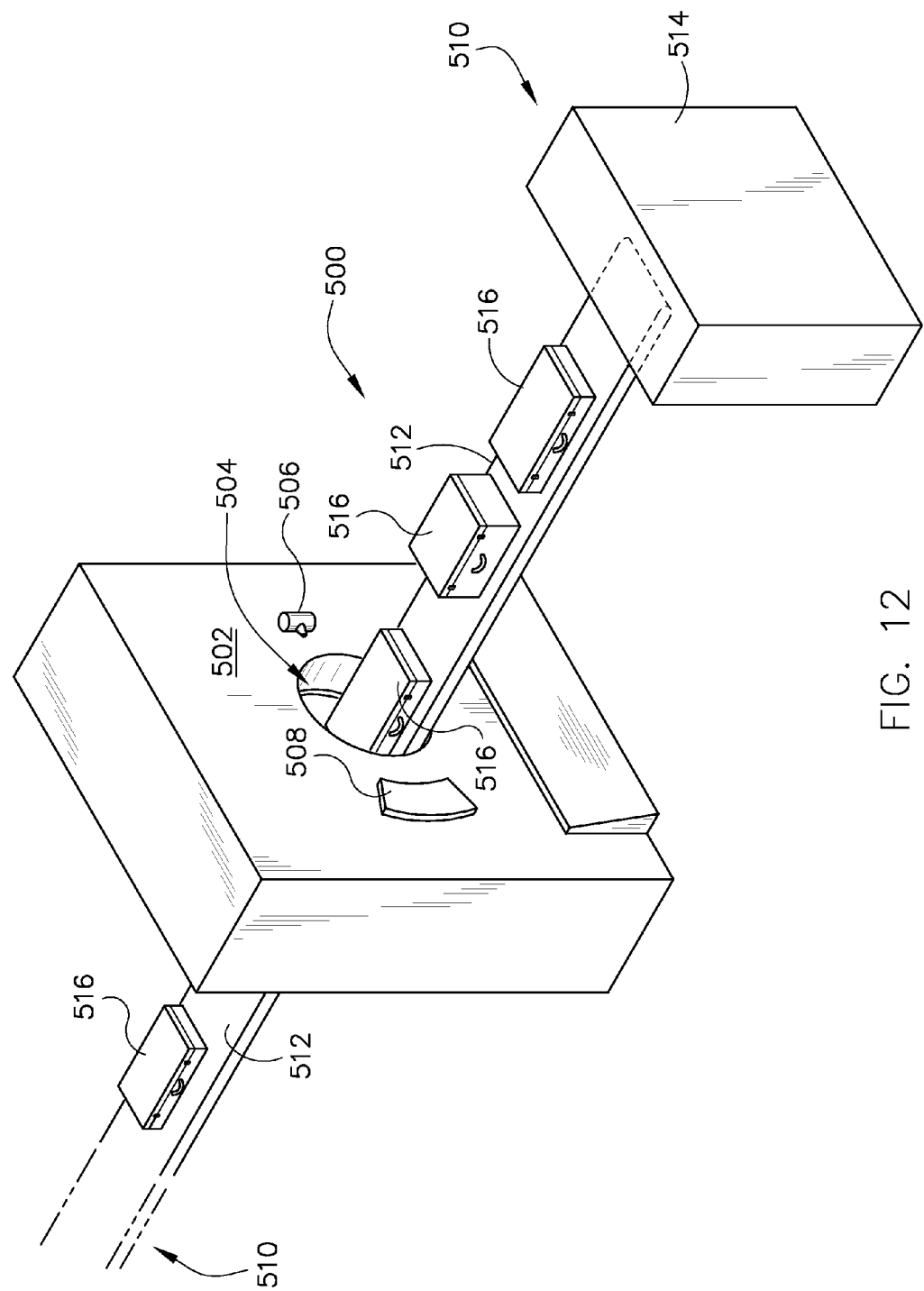
FIG. 12 is a pictorial view of a CT system for use with a non-invasive package inspection system.

Referring now to FIG. 12, package/baggage inspection system 500, incorporating embodiments of the invention, includes a rotatable gantry 502 having an opening 504 therein through which packages or pieces of baggage may pass. The rotatable gantry 502 houses a high-frequency electromagnetic energy source 506 as well as a detector assembly 508 semiconductor radiation detector elements, such as CZT detector elements similar to that shown in FIG. 6 or 7. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

Exemplary embodiments of the invention are disclosed with respect to use of the event timing circuit in a data acquisition system for radiation detectors. However, one skilled in the art will recognize that the invention is not limited to these embodiments, and may also be employed in other applications in which it is advantageous to time stamp asynchronous events.

A technical contribution for the disclosed method and apparatus is that it provides for a controller implemented acquisition and processing of electronic data from a radiation detector.

According to one embodiment of the invention, an event time stamping system comprising a current source, an integrator comprising an input and an output, and configured to output a voltage proportional to the length of time the current source is coupled to the input, and one or more switches configured to couple the current source to the input of the integrator upon receipt of an event signal and configured to de-couple the current source from the input of the integrator upon receipt of a control trigger. The system further comprises a lock-out signal generator configured to generate a lock-out signal, and a controller coupled to the one or more switches, wherein the controller is configured to generate the control trigger based on the lock-out signal to ensure a minimum integration time.

In accordance with another embodiment of the invention, a method of manufacturing that includes providing a current source, providing an operational transconductance amplifier having an input and an output, coupling an integrating capacitor between the input and the output of the amplifier, and coupling one or more switches between the current source and the integrating capacitor. The method further includes coupling a controller to the one or more switches, and configuring the controller to control the one or more switches to de-couple the current source from the integrating capacitor after at least a minimum integration time.

According to yet another embodiment of the invention, a time-to-voltage converter comprising a current source, a feedback capacitor, an operational transconductance amplifier having an output coupled to the feedback capacitor, and one or more switches configured to couple the current source to the feedback capacitor upon receipt of an event trigger, and configured to de-couple the current source from the feedback capacitor after a minimum determined time period.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. An event time stamping system comprising:
a current source;
an integrator comprising an input and an output, wherein the current source is coupled to the input and the output is configured to provide a voltage proportional to a length of time;
one or more switches configured to couple the current source to the input of the integrator upon receipt of an event signal and configured to de-couple the current source from the input of the integrator upon receipt of a control trigger;

a lock-out signal generator configured to generate a lock-out signal; and a controller coupled to the one or more switches comprising a clock signal generator configured to generate a system clock signal, wherein the controller is configured to generate the control trigger based on the lock-out signal to provide a minimum integration time wherein the minimum integration time comprises a time period of a phase shift between the system clock signal and the lock-out signal.

2. The system of claim 1, wherein the controller generates the control trigger based on the lock-out signal to provide a maximum integration time comprising a sum of the time period of the phase shift between the system clock signal and the lock-out signal and the time period of one complete clock cycle.

3. The system of claim 1, wherein the integrator comprises: an operational transconductance amplifier comprising an input coupled to the input of the integrator and an output coupled to the output of the integrator; and a first integrating capacitor coupled to the input and to the output of the operational transconductance amplifier.

4. The system of claim 1, wherein the integrator comprises a reset switch coupled in parallel with the first integrating capacitor.

5. The system of claim 1, wherein the integrator comprises: a plurality of integrating capacitors; and a plurality of switches coupled to the plurality of integrating capacitors and configured to selectively couple and de-couple each of the plurality of integrating capacitors with the first integrating capacitor.

6. The system of claim 1, comprising: an analog-to-digital converter comprising: a comparator configured to receive an input from a reference signal generator comprising: a first input coupled to the output of the integrator; a second input coupled to the reference signal generator; and an output configured to change states; a digitizing counter configured to start counting upon receipt of a signal from the controller; and a register coupled to the comparator and to the digitizing counter, and configured to latch a value from the digitizing counter when the output of the comparator changes state.

7. The system of claim 4, wherein the reference signal generator is configured to supply an analog ramp signal to the second input of the comparator.

8. A method of manufacturing comprising:
providing a current source;
providing an operational transconductance amplifier having an input and an output;
coupling an integrating capacitor between the input and the output of the amplifier;
coupling one or more switches between the current source and the integrating capacitor;
coupling a controller to the one or more switches; and
configuring the controller to control the one or more switches to de-couple the current source from the integrating capacitor after at least a minimum integration time wherein the minimum integration time comprises the time period of the phase shift between a lock-out signal and a clock signal generated by a lock-out signal generator and a clock signal generator respectively.

9. The method of claim 8, comprising coupling a reset switch in parallel with the integrating capacitor.

10. The method of claim 8, comprising coupling a plurality of parallel integrating capacitors to the output of the amplifier and to the input of the amplifier.

11. The method of claim 10, comprising configuring at least one of the plurality of parallel integrating capacitors such that the at least one integrating capacitor can be disconnected from the amplifier.

12. The time-to-voltage converter of claim 10, wherein the minimum determined time period comprises the phase-shift time period between the clock signal and a lock-out signal.

13. The time-to-voltage converter of claim 10, wherein a maximum determined time period comprises a sum of the phase-shift time period between the clock signal and the lock-out signal and the time period of one cycle of the clock signal.

14. The time-to-voltage converter of claim 9, comprising a reset switch connected in parallel with the feedback capacitor.

15. A time-to-voltage converter comprising:
a current source;
a feedback capacitor;
an operational transconductance amplifier having an output coupled to the feedback capacitor; and
one or more switches configured to couple the current source to the feedback capacitor upon receipt of an event trigger, and configured to de-couple the current source from the feedback capacitor after a minimum determined time period wherein the one or more switches are controlled b a controller configured to generate a clock signal and by a lock-out signal which is phase-shifted from the clock signal.

16. The time-to-voltage converter of claim 9, comprising a plurality of parallel feedback capacitors.

17. The time-to-voltage converter of claim 15, comprising one or more switches in series with a respective one of the plurality of parallel feedback capacitors, the one or more switches configured to disconnect the respective one of the plurality of feedback capacitors from the amplifier.

* * * * *